United States Patent
Fouts et al.

(10) Patent No.: US 6,572,747 B1
(45) Date of Patent: Jun. 3, 2003

(54) METHOD FOR MAKING A WIDE RANGE SENSOR ELEMENT

(75) Inventors: Richard Eugene Fouts, Grand Blanc, MI (US); Lora B. Younkman, Grand Blanc, MI (US); Raymond Leo Bloink, Swartz Creek, MI (US); Kaius Kiiren Polikarpus, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/264,509

(22) Filed: Mar. 8, 1999

(51) Int. Cl.$^7$ .............................................. G01N 27/407
(52) U.S. Cl. .................... 204/426; 204/424; 156/89.12; 156/89.16
(58) Field of Search ................. 204/424, 425, 204/426; 156/89.12, 89.16

(56) References Cited

U.S. PATENT DOCUMENTS

| | | | |
|---|---|---|---|
| 3,007,222 A | | 11/1961 | Ragan ........................ 25/156 |
| 4,487,680 A | * | 12/1984 | Logothetis et al. ......... 204/426 |
| 4,508,841 A | | 4/1985 | Onuma et al. ................ 502/73 |
| 4,943,330 A | | 7/1990 | Iino et al. ..................... 156/89 |
| 5,169,513 A | * | 12/1992 | Mase et al. ................. 204/429 |
| 5,288,375 A | * | 2/1994 | Logothetis et al. ......... 204/425 |
| 5,329,806 A | | 7/1994 | McClanahan et al. ..... 73/31.05 |
| 5,360,528 A | | 11/1994 | Oh et al. .................... 204/425 |
| 5,384,030 A | | 1/1995 | Duce et al. ................. 204/426 |
| 5,467,636 A | | 11/1995 | Thompson et al. ........ 73/23.31 |
| 5,480,535 A | * | 1/1996 | Kondo et al. ............... 204/425 |
| 5,518,603 A | | 5/1996 | Furuhashi et al. .......... 204/429 |
| 5,522,979 A | | 6/1996 | Tatumoto et al. ........... 204/429 |
| 5,762,737 A | * | 6/1998 | Bloink et al. ............. 156/89.12 |
| 5,895,591 A | * | 4/1999 | Kojima et al. .............. 219/209 |

OTHER PUBLICATIONS

"Function and Design ZrO$_2$ Exhaust Oxygen Sensors", Chapter 2 month, year unavailable.

"Air–Fuel Ratio Sensor Utilizing Ion Transportation in Zirconia Electrolyte", by Takao Sasayama and Teruo Yamauchi (Hitachi America, Ltd.), Robert Byers (Hitachi Farmington Hills Technical Center), and Seikoo Suzuki and Sadayasu Ueno (Hitachi, Ltd.) month, year unavailable.

"Tape Casting: The Basic Process for Meeting the Needs of the Electronics Industry", by Richard E. Mistler (Keramos Industries, Inc., Morrisville, Pennsylvania 19067. 1990 month unavailable.

"Tape Casting" by Richard E. Mistler (Keramos Industries, Inc.) Reprinted from Engineered Materials Handbook, vol. 4: Ceramics and Glasses month, year unavailable.

* cited by examiner

Primary Examiner—Robert J. Warden, Sr.
Assistant Examiner—Kaj K. Olsen
(74) Attorney, Agent, or Firm—Vincent A. Cichosz

(57) ABSTRACT

The method of making a wide range oxygen sensor of the present invention enables ease of handling and processing, particularly in a mass production environment. This process comprises forming planar composite elements of the sensor where the elements are individually laminated. These laminated composites are easily handled and readily stacked. Furthermore, electrodes and electrode leads can be readily deposited on the laminated composites, across the intersection of the various materials forming the composite. After deposition of the electrodes, leads, and a heater, the elements are stacked accordingly and laminated to produce the oxygen sensor.

11 Claims, 4 Drawing Sheets

METHOD FOR MAKING A WIDE RANGE SENSOR ELEMENT

TECHNICAL FIELD

The present application relates to patent application U.S. Ser. No. 09/264,510, filed concurrently with this application, which is hereby incorporated by reference.

The present invention relates to wide range oxygen sensors and especially relates to a simplified wide range oxygen sensor design.

BACKGROUND OF THE INVENTION

Oxygen sensors are used in a variety of applications which require qualitative and quantitative analysis of gases. In automotive applications, the direct relationship between oxygen concentration in the exhaust gas and air to the fuel ratio of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically consists of an ionically conductive solid electrolyte material, a porous electrode on the sensor's exterior exposed to the exhaust gases with a porous protective overcoat, and a porous electrode on the sensor's interior surface exposed to a known oxygen partial pressure. Sensors typically used in automotive applications use a yttria stabilized zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wall, according to the Nernst equation:

$$E = \left(\frac{RT}{4F}\right) \ln\left(\frac{P_{O_2}^{ref}}{P_{O_2}}\right)$$

where:

E=electromotive force
R=universal gas constant
F=Faraday constant
T=absolute temperature of the gas
$P_{O_2}^{ref}$=oxygen partial pressure of the reference gas
$P_{O_2}$=oxygen partial pressure of the exhaust gas Due to the large difference in oxygen partial pressure between fuelrich and fuellean exhaust conditions, the electromotive force changes sharply at the stoichiometric point, giving rise to the characteristic switching behavior of these sensors. Consequently, these potentiometric oxygen sensors indicate qualitatively whether the engine is operating fuelrich of fuellean, without quantifying the actual air to fuel ratio of the exhaust mixture.

Increased demand for improved fuel economy and emissions control has necessitated the development of oxygen sensors capable of quantifying the exhaust oxygen partial pressure over a wide range of air fuel mixtures in both fuel-rich and fuel-lean conditions. As is taught by U.S. Pat. No. 4,863,584 to Kojima et al., U.S. Pat. No. 4,839,018 to Yamada et al., U.S. Pat. No. 4,570,479 to Sakurai et al., and U.S. Pat. No. 4,272,329 to Hetrick et al., an oxygen sensor which operates in a diffusion limited current mode produces a proportional output which provides a sufficient resolution to determine the air-to-fuel ratio under fuel-rich or fuel-lean conditions. Generally, diffusion limited current oxygen sensors have a pumping cell and a reference cell with a known internal or external oxygen partial pressure reference. A constant electromotive force, typically corresponding to the stoichiometric electromotive force, is maintained across the reference cell by pumping oxygen through the pumping cell. The magnitude and polarity of the resulting diffusion limited current is indicative of the exhaust oxygen partial pressure and, therefore, a measure of air-to-fuel ratio.

As is taught by U.S. Pat. No. 4,450,065, wide range oxygen sensors commonly employ an aperture with a cross-sectional area to length ratio sufficiently small to limit exhaust gas diffusion. In this sensor, a gap between the pumping and reference cells forms such an aperture and limits diffusion of exhaust gas to a common environment between the two cells. This common environment, or diffusion chamber is required in an aperture construction for adequate mixing of the diffused exhaust gas; however, it tends to slow the frequency response of the sensor operation. Additionally, although the two electrodes adjacent to the diffusion chamber can be shorted together to eliminate one lead, four separate electrodes are required in this construction.

Commonly assigned U.S. Pat. No. 5,360,528 to Oh et al., teaches a wide range oxygen sensor having improved mass production capabilities. This wide range oxygen sensor employs a porous layer, formed by plasma spray deposition, to limit oxygen diffusion in lieu of the diffusion limiting aperture. Referring to FIG. 1, this wide range oxygen sensor 16 has a planar structure with a single solid electrolyte layer 6 shared by electrochemical storage (4/10/6/8), pumping (2/12/6/14) and reference (10/6/12) cells. The electrochemical pumping cell has a diffusion layer 2 formed from a porous ceramic to permit diffusion of oxygen molecules through this layer.

Although the wide range oxygen sensor of Oh et al. eliminates the need for a mixing chamber between the pumping and reference cells and improves mass production capabilities thereof, there still exists a need to further improve the processing and assembly of wide range oxygen sensors in mass production.

SUMMARY OF THE INVENTION

The present invention relates to methods for producing oxygen sensors. In one embodiment the method comprises: preparing a planar first electrolyte layer having a portion of first electrolyte tape and a portion of first substrate material tape wherein at least one edge of said first electrolyte tape abuts said first substrate material tape; laminating said first electrolyte layer; depositing an outer electrode on said laminated first electrolyte layer, depositing an inner electrode on a solid electrolyte layer, depositing a reference electrode on a reference electrode layer; depositing a heater on a heater side of a heater layer, stacking said solid electrolyte layer and said first electrolyte layer such that said inner electrode is disposed therebetween, in contact with both said solid electrolyte and said first electrolyte, disposing a first side of said reference electrode layer adjacent to said solid electrolyte layer such that said reference electrode is in contact with said solid electrolyte, disposing said heater side of said heater layer on a second side of said reference electrode layer, and laminating said first electrolyte layer, said solid electrolyte layer, said reference electrode layer and said heater layer together.

In another embodiment the method comprises: preparing a planar layer having a first portion of first material tape and a second portion of second material tape, wherein at least one edge of the first material tape abuts at least another edge of the second material tape; compressing said first planar layer to form a single planar piece, wherein the first and second materials are coplanar and have an interface between said one edge and said another edge; depositing a conductive material on a first side of said single planar piece across the interface; stacking said first side and/or a second side of said single planar piece with at least one additional planar piece; laminating said stacked single planar piece and said at least one additional planar piece; and sintering the laminated and stacked single planar piece and at least one additional piece.

These and other objects, features and advantages of the present invention will be apparent from the following brief description of the drawings, detailed description, and appended claims and drawings.

BRIEF DESCRIPTION OF THE DRAWINGS

The present invention will now be described, by way of example only, with reference to the accompanying drawings which are meant to be exemplary, not limiting, and wherein like elements are numbered alike in several FIGURES, in which.

DESCRIPTION OF THE PREFERRED EMBODIMENT

Figure 1:
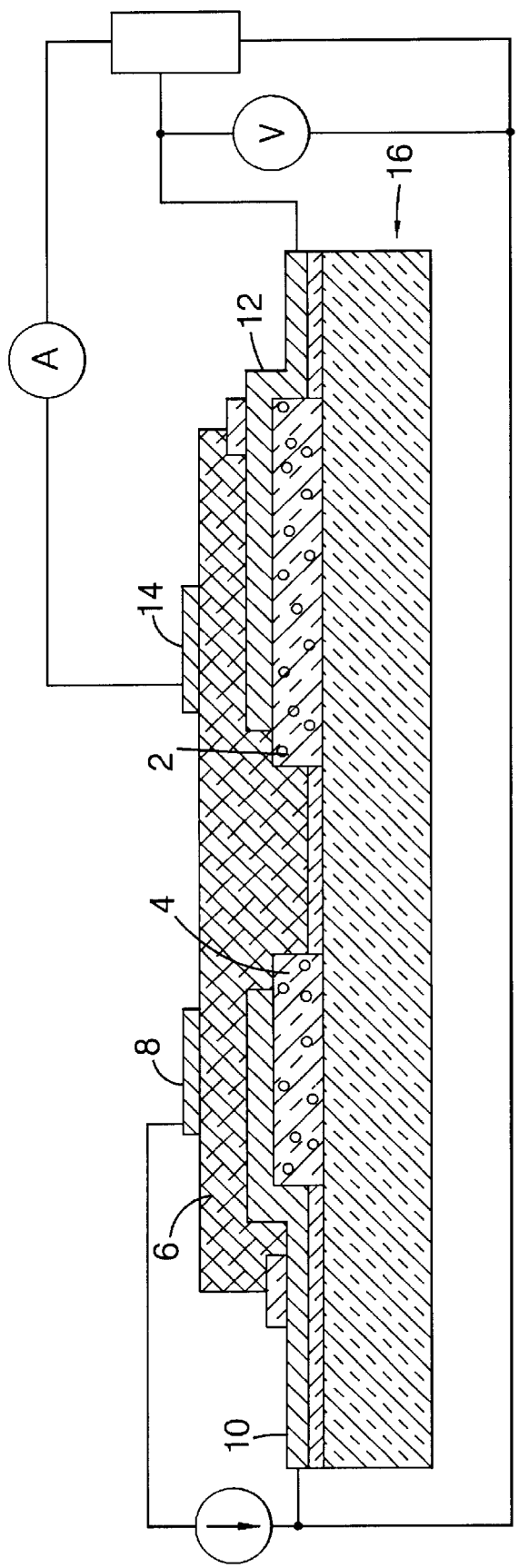
FIG. 1 is a cross sectional view of the four electrode wide range oxygen sensor of Oh et al.

The present invention relates to a unique, simplified, process for making a wide range oxygen sensor, comprising: first individually laminating each composite layer, depositing the electrodes onto the appropriate layers, and then stacking, laminating and co-firing the stack to form the oxygen sensor.

The solid electrolyte layer can be formed of any material capable of permitting the electrochemical transfer of oxygen ions while inhibiting the physical passage of any exhaust gases, which has an ionic/total conductivity ratio of approximately unity, and which is compatible with the environment in which the sensor will be utilized. Possible solid electrolyte materials include conventional materials such as yttria stabilized zirconia, calcia stabilized zirconia, and magnesia stabilized zirconia, among others. Typically, the solid electrolyte has a thickness of up to about 500 microns with a thickness of approximately 25 microns to about 500 microns preferred. Although this layer can be formed via many conventional processes including, but not limited to, die pressing, roll compaction, stenciling and screen printing, for improved process compatibility, it is preferred to utilize a tape process using known ceramic tape casting methods.

As with the solid electrolyte, the porous electrolyte makes use of an applied electrical potential to influence the movement of oxygen. The porous electrolyte should be capable of permitting the physical migration of exhaust gas, the electrochemical movement of oxygen ions therethrough, and be compatible with the environment in which the sensor is utilized. Possible porous electrolytes include, but are not limited to, zirconia base electrolytes, such as yttria stabilized zirconia, calcia stabilized zirconia, magnesia stabilized zirconia, and others, having a porosity sufficient to enable the physical movement of exhaust gas therethrough, while limiting the current output of the oxygen sensor under relatively extreme fuel-rich or fuel-lean conditions. Typically the porosity ranges up to about 20%, with a median pore size of up to about 0.5 microns. Commonly assigned U.S. Pat. No. 5,762,737 to Bloink et al., which is hereby incorporated by reference, further explains the porous electrolyte. Alternatively, porous electrolyte can be replaced with a solid electrolyte having one or more perforations, holes, slits, or apertures therein so as to enable the physical passage of exhaust gases.

The various electrodes disposed in contact with the solid electrolyte and the porous electrolyte, can be comprised of any catalyst capable of ionizing oxygen, including, but not limited to, noble metal catalysts such as platinum, palladium and others, including alloys. The electrodes have a porosity sufficient to permit the diffusion of oxygen and exhaust gas molecules therethrough without substantially restricting such gas diffusion, and a thickness sufficient to attain the desired catalytic activity. Typically a porosity equal to or greater than the porosity of the porous electrolyte and a thickness of approximately 1.0 to about 25 microns can be employed, with a thickness of about 10 to about 20 microns preferred.

The electrodes can be formed using conventional techniques such as sputtering, chemical vapor deposition, screen printing, and stenciling, among others, with screen printing the electrodes onto appropriate tapes preferred due to simplicity, economy, and compatibility with the subsequent co-fired process. For example, reference electrode 24 can be screen printed onto layer 42 or onto the solid electrolyte 20, with inner electrode 22 screen printed onto solid electrolyte 20, and outer electrode 30 screen printed onto porous electrolyte layer 32/40 or protective layer 36/34. (See FIG. 2)

Although the porosity of the reference electrode 24 is typically sufficient to hold an adequate quantity of oxygen to act as a reference, a space 38 can be provided between the reference electrode 24 and the layer 42. This space can be formed by depositing a carbon base material between the reference electrode 24 and the layer such that upon processing the carbon burns out, leaving a space.

Layers 28, 34, 40, 42, 44, 46, 48, 52 and 58 are dielectric materials which effectively protect various portions of the sensor while functioning as separators and substrates. Layer 28 inhibits electrical contact between solid electrolyte 20 and porous electrolyte 32, and layers 42, 44, 46, and 48 electrically isolate the heater circuit from the sensor circuits, while layers 34 and 52 physically cover the outer electrode 30 and heater circuit 50 to provide physical protection, e.g., against abrasion, and to electrically isolate these components from the packaging.

Preferably, these layers are comprised of material having substantially similar coefficients of thermal expansion, shrinkage characteristics and chemical compatibility, to at least minimize, if not eliminate, delamination and other processing problems. Typically these layers are composed of alumina or another dielectric material capable of inhibiting electrical communication and providing physical protection. These layers can be up to about 500 microns thick with a thickness of about 50 to about 200 microns preferred. Similar to the solid and porous electrolytes, these layers can be formed using ceramic tape casting methods or other methods such as plasma spray deposition techniques, screen printing, stenciling and others conventionally used in the art.

The layer 28 disposed between the inner electrode 22 and the porous electrolyte layer 32/40 has an opening 26 therein which enables exhaust gases to contact inner electrode 22 and defines pumping cell 30/32/22. The opening 26 should have a size and geometry substantially similar to the size and geometry of inner electrode 22 so as to enable exposure of substantially all of the active area of inner electrode 22 to exhaust gas while inhibiting contact and ionic leakage between the porous and solid electrolytes.

The heater 50 can be any conventional heater capable of maintaining the oxygen sensor at a sufficient temperature to facilitate the various electrochemical reactions therein. Typically the heater, which is a metal such as platinum, platinum-alumina, palladium, platinum-palladium, among others, or alloys thereof, is generally screen printed onto a substrate to a thickness of about 5 to about 50 microns.

Figure 2:
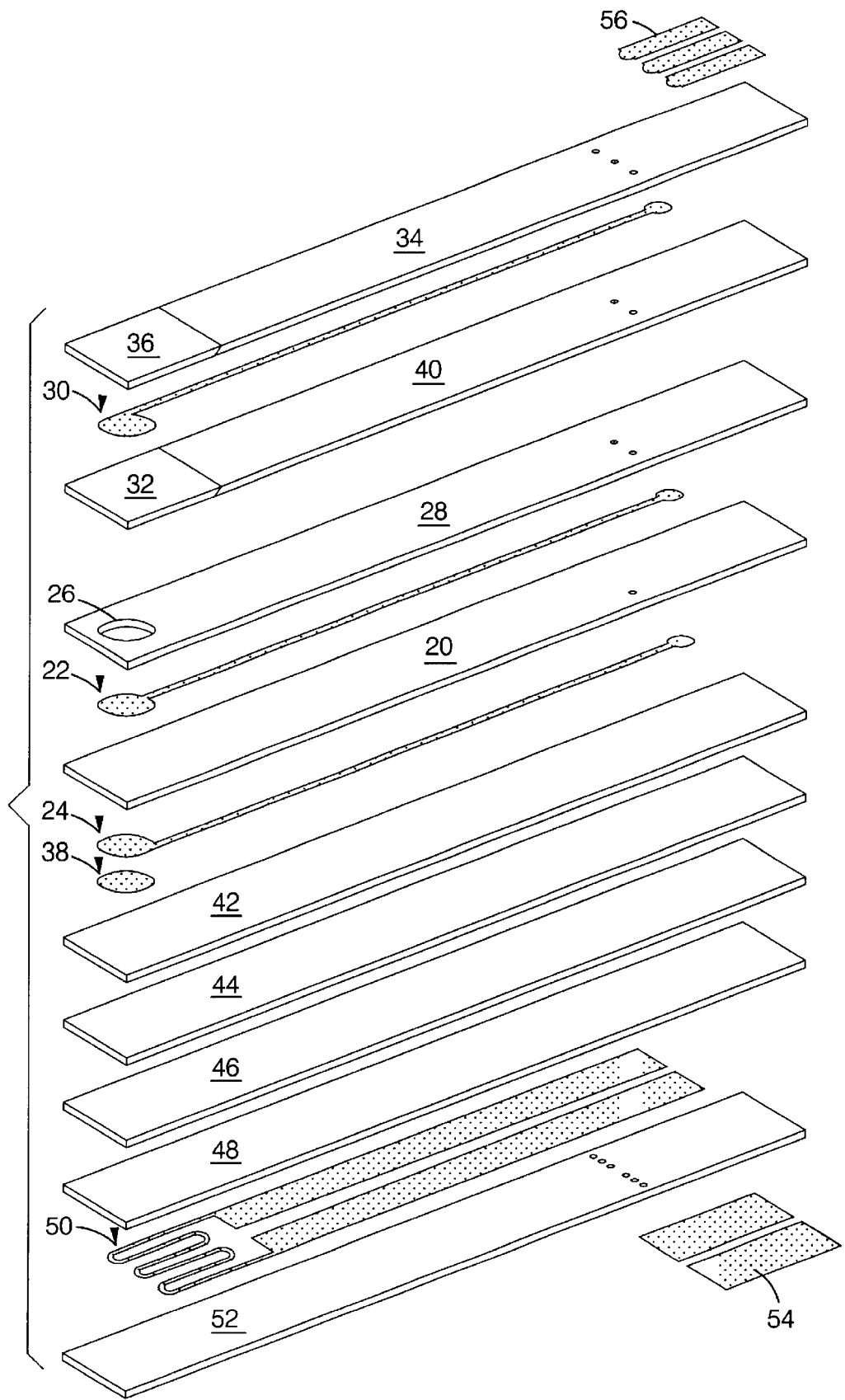
FIG. 2 is a detailed, expanded view of one embodiment of a three electrode wide range oxygen sensor which can be produced using the process of the present invention.
Figure 3:
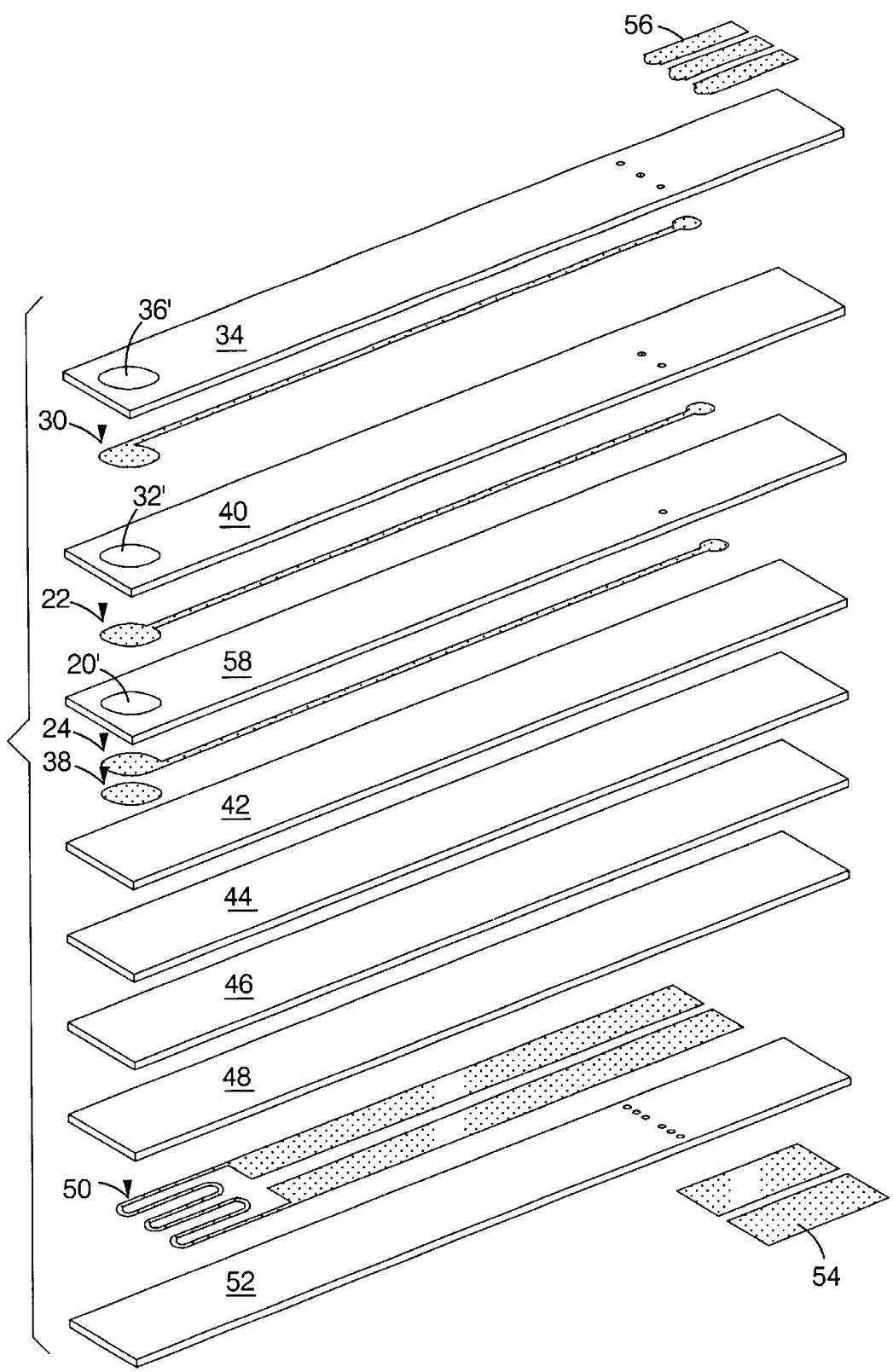
FIG. 3 is a detailed, expanded view of another embodiment of a three electrode wide range oxygen sensor which can be produced using the process of the present invention.

In a preferred embodiment of the present invention shown in FIG. 3, the porous electrolyte 32', solid electrolyte 20', and porous protective material 36' are in the form of disks disposed in holes through layers 40, 58 and 34, respectively. This arrangement eliminates the use of excess porous electrolyte, solid electrolyte and porous protective material, and reduces the size of the sensor by eliminating a layer. With this arrangement, layer 28 is a alminated (See FIG. 2)

During oxygen sensor production, each composite tape is individually prepared and laminated prior to assembling the sensor. In one embodiment, preparation of an individual tape comprises aligning an edge of the porous electrolyte, for example, with an insulating tape of appropriate size and dimension. The tape is then laminated, preferably isostatically, to bond the edge of the porous electrolyte to the edge of the insulating tape, thereby forming a single composite tape. Lamination can proceed at a temperature of up to about 100° C. and a pressure of about 4,000 pounds per square inch ("psi"), for a period of up to about 15 minutes, with a temperature of about 80° C. to about 90° C. and a pressure of about 1,500 psi to about 2,500 psi for a period of about 4 minutes to about 10 minutes preferred. In another embodiment, if the porous electrolyte is to be disposed within the tape, a hole is formed in the tape and a disk of porous electrolyte having an appropriate size and geometry is formed. The porous electrolyte having substantially the same size and geometry as the hole is then placed in the hole and the tape is laminated as described above. This process is repeated for each composite, i.e., multi-material layer.

The electrodes and heater can then be deposited onto the appropriate layers. For example, the outer electrode can be deposited onto the laminated layer 36'/34 or 32'/40 such that the outer electrode 30 contacts the porous protective material 36' or porous electrolyte 32', accordingly. (See FIG. 3) The inner electrode 22 can be deposited onto a second side of the laminated porous electrolyte layer 32'/40 or on the laminated solid electrolyte layer 20'/58 such that the inner electrode 22 is in contact with the porous electrolyte 32' or solid electrolyte 20', accordingly. The reference electrode 24 is deposited on an opposite side of the laminated layer 20'/58 or on layer 42 such that the reference electrode 24 contacts the solid electrolyte 20' or can be aligned therewith, accordingly. Finally, the heater 50 is deposited on layer 48 or 52.

Once all of the layers have been prepared, they are stacked accordingly. For example, FIG. 3 shows one embodiment of the present invention where the sensor is stacked as follows: laminated layers 36'/34 having porous protective material 36'; laminated layer 32'/40 with porous electrolyte 32' oriented in contact with outer electrode 30 which, in turn, contacts porous protective material 36'; laminated layer 20'/58 is aligned such that the inner electrode 22 contacts both the solid electrolyte 20' and the porous electrolyte 32'; substrates are then aligned with the laminated layer 20'/58 such that the reference electrode 24 contacts the solid electrolyte 20' and is separated from the heater 50 by at least one layer 48, with the heater 50 disposed between layers 48 and 52.

The stack is then laminated, preferably isostatically, at a temperature and pressure, and for a period of time sufficient to bond the various layers together and to eliminate any void spaces therebetween. Typically the stack is laminated for up to about 15 minutes, at a temperature of up to about 100° C. and a pressure of up to about 4,500 psi, with a time of about 10 minutes, temperature of about 80° C. to about 90° C., and a pressure of about 3,500 psi to about 4,000 psi preferred.

Figure 4:
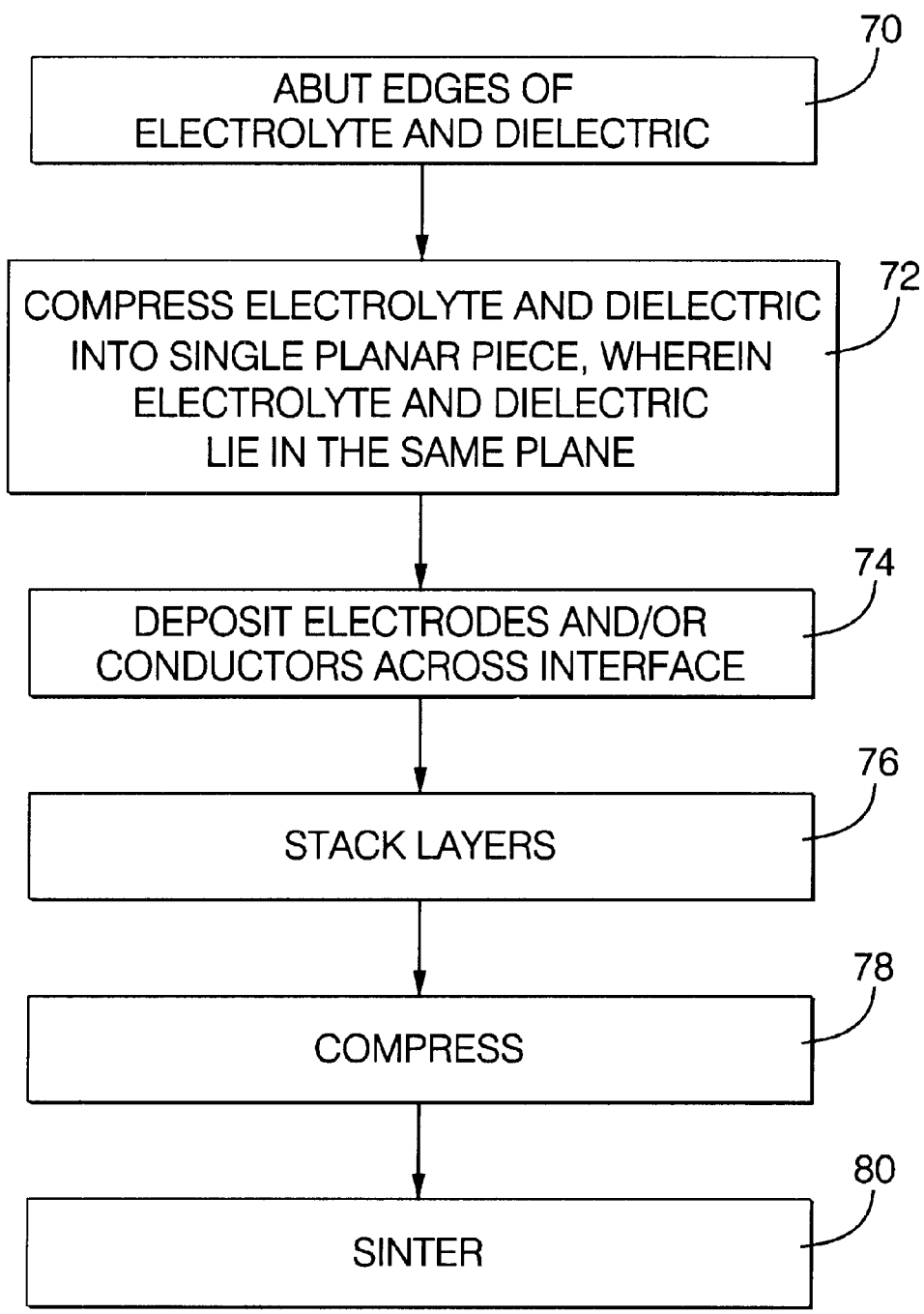
FIG. 4 illustrates steps of an example method of this invention.

Referring now to FIG. 4, example steps of this invention begin at step 70, where edges of the green bodies of the two different materials to be laminated into a coplanar piece, for example, of electrolyte 32 and dielectric 40 (FIG. 2) are placed into abutting contact with each other. At step 72, the green bodies with the abutting edges are isostatically compressed to form a single planar piece, wherein the two materials, for example electrolyte 32 and dielectric 40, are now part of the single planar piece and each lie in the same plane as the other. At step 74, the electrodes and/or conductors are added to the single planar piece, spanning the interface between the two materials that now make up the single planar piece. The advantage obtained is that the electrode/conductor spanning the interface will not fracture or become disconnected at the interface, as may occur if the two materials are not first laminated into the single planar piece. The steps 72–74 are repeated for other layers formed from two different materials in the same plane.

Step 76 comprises the stacking of the single planar piece with other layers as appropriate to complete the sensor construction, for example as shown in FIGS. 2 and 3. And steps 78 and 80 comprise the isostatic laminadion and the sintering as is generally known to those skilled in the art.

Unlike prior art wide range oxygen sensors, the sensor of the present invention utilizes three electrodes to form a pumping cell, reference cell, and an oxygen storage chamber. Typical prior art sensors require four electrodes to perform the same function. Consequently, the sensor of the present invention is a simplified, unique sensor which is more suitable for mass production.

In addition to utilizing a reduced number of electrodes, one embodiment of the sensor of the present invention substantially limits the amount of the different materials employed, i.e., the majority of the sensor is preferably the same material, such as the substrate/insulator material, with the amount of electrolyte and other materials needed substantially reduced. The present invention further minimizes the total interface area between the electrolyte and non-electrolyte materials, thereby reducing stresses relating to different shrinkage factors and different coefficients of thermal expansion, maximizing the electrical isolation between all of the circuits, and reducing cross-talk. Consequently, the sensor of the present invention has substantially eliminated production problems such as stress, delamination, cracking due to differing coefficients of thermal expansion, chemical bonding problems, and improved sensitivity by reducing cross-talk.

Finally, the sensors of the present invention simplify the use of composite tape by laminating each composite tape individually prior to stack processing. This enables deposition of the electrodes and leads, for example, across the interface of the two materials in the composite, thereby simplifying preparation, and improving the contact between the leads and the electrodes which are in electrical communication.

It will be understood that a person skilled in the art may make modifications to the preferred embodiment shown herein within the scope and intent of the claims. While the present invention has been described as carried out in a specific embodiment thereof, it is not intended to be limited thereby but is intended to cover the invention broadly within the scope and spirit of the claims.

What is claimed is:

1. A method for producing an oxygen sensor, comprising:
   preparing a first electrolyte layer by forming a hole in a first material, said hole having a first hole geometry and first hole size;
   disposing a first electrolyte in said first hole, wherein said first electrolyte has a first electrolyte geometry and a electrolyte size substantially equivalent to said first hole geometry and said first hole size;
   laminating said first electrolyte layer;
   forming a hole in said second material, said hole having a second hole geometry and second hole size;
   disposing a solid electrolyte in said second hole, wherein said solid electrolyte has a solid electrolyte geometry and a solid electrolyte size substantially equivalent to said second hole geometry and said second hole size;
   depositing an outer electrode on said laminated first electrolyte layer;
   depositing an inner electrode on a solid electrolyte layer;
   depositing a reference electrode on a reference electrode layer;
   depositing a heater on a heater side of a heater layer;
   stacking said solid electrolyte layer and said first electrolyte layer such that said inner electrode is disposed therebetween, in contact with both said solid electrolyte and said first electrolyte, and in ionic communication with said outer electrode;
   disposing a first side of said reference electrode layer adjacent to said solid electrolyte layer such that said reference electrode is in contact with said solid electrolyte;
   disposing said heater side of said heater layer on a second side of said reference electrode layer; and
   laminating said first electrolyte layer, said solid electrolyte layer, said reference electrode layer and said heater layer together.

2. A method for producing an oxygen sensor as in claim 1, wherein said first material tape, said second material tape, said reference electrode layer, and said heater layer are chemically compatible materials.

3. A method for producing an oxygen sensor as in claim 1, wherein said first material tape, said second material tape, said reference electrode layer, and said heater layer comprise alumina.

4. A method for producing an oxygen sensor comprising:
   forming a first hole in a first material tape, said first hole having a first hole geometry and first hole size, wherein a first electrolyte tape has a first electrolyte geometry and a first electrolyte size substantially equivalent to said first hole geometry and said first hole size;
   disposing said first electrolyte tape in said first hole, wherein a first edge defining a thickness of said first electrolyte tape abuts a second edge defining a thickness of said first material tape;
   laminating to form said first electrolyte layer;
   depositing an outer electrode on a first side of said laminated first electrolyte layer;
   forming a second hole in a second material tape, said second hole having a second hole geometry and second hole size, wherein a solid electrolyte tape has a solid electrolyte geometry and a solid electrolyte size substantially equivalent to said second hole geometry and said second hole size;
   disposing said solid electrolyte tape in said second hole, wherein a first edge of said second material tape abuts a second edge defining a thickness of said solid electrolyte tape;
   laminating to form said solid electrolyte layer
   depositing an inner electrode on a first side of said solid electrolyte layer and a reference electrode on a second side of said solid electrolyte layer such that said inner electrode and said reference electrode are in electrical communication;
   depositing a heater on a heater side of a heater layer;
   stacking said solid electrolyte layer and said first electrolyte layer such that said inner electrode is disposed therebetween, in contact with both said solid electrolyte layer and said first electrolyte layer;
   disposing said heater side of said heater layer on said second side of said solid electrolyte layer; and
   laminating said first electrolyte layer, said solid electrolyte layer, and said heater layer together.

5. A method for producing an oxygen sensor as in claim 4, wherein said first material tape, said second material tape, said reference electrode layer, and said heater layer are chemically compatible materials.

6. A method for producing an oxygen sensor as in claim 4, wherein said first material tape, said second material tape, said reference electrode layer, and said heater layer are alumina.

7. A method for producing an oxygen sensor, comprising:
   forming a first hole in said first material tape, said first hole having a first hole geometry and first hole size, wherein a first electrolyte tape has a first electrolyte geometry and a first electrolyte size substantially equivalent to said first hole geometry and said first hole size;
   disposing said first electrolyte tape in said first hole, wherein at least one edge of said first electrolyte tape abuts said first material tape;
   laminating to form said first electrolyte layer;
   forming a second hole in said second material tape, said second hole having a second hole geometry and second hole size, wherein a solid electrolyte tape has a solid electrolyte geometry and a solid electrolyte size substantially equivalent to said second hole geometry and said second hole size;
   disposing said solid electrolyte tape in said second hole, wherein a portion of a second material tape abuts at least one edge of said solid electrolyte tape;
   laminating said solid electrolyte layer;
   depositing an outer electrode on said laminated first electrolyte layer;
   depositing an inner electrode on said solid electrolyte layer;

depositing a reference electrode on a reference electrode layer;

depositing a heater on a heater side of a heater layer;

stacking said solid electrolyte layer and said first electrolyte layer such that said inner electrode is disposed therebetween, in contact with both said solid electrolyte layer and said first electrolyte layer, and in ionic communication with said outer electrode;

disposing a first side of said reference electrode layer adjacent to said solid electrolyte layer such that said reference electrode is in contact with said solid electrolyte layer;

disposing said heater side of said heater layer on a second side of said reference electrode layer; and laminating said first electrolyte layer, said solid electrolyte layer, said reference electrode layer, and said heater layer together.

8. A method for producing an oxygen sensor, comprising:

preparing a first electrolyte layer by forming a first hole in a first material tape, said first hole having a first hole geometry and first hole size;

disposing a first electrolyte tape in said first hole, wherein said first electrolyte tape has a first electrolyte geometry and a first electrolyte size substantially equivalent to said first hole geometry and said first hole size;

compressing said first electrolyte layer;

disposing an outer electrode in communication with a first side of said first electrolyte; and disposing an inner electrode in communication with a second side of said first electrolyte tape, wherein said inner electrode is in ionic communication with said outer electrode.

9. A method for producing an oxygen sensor as in claim 8, further comprising:

forming a second hole in a second material tape, said second hole having a second hole geometry and second hole size;

disposing a solid electrolyte tape in said second hole to form a solid electrolyte layer, wherein said solid electrolyte tape has a solid electrolyte geometry and a solid electrolyte size substantially equivalent to said second hole geometry and said second hole size;

compressing said solid electrolyte layer;

disposing said solid electrolyte tape in communication with said inner electrode;

disposing a third electrode on a side of said solid electrolyte tape opposite said inner electrode to form a stack; and laminating said stack.

10. A method for producing an oxygen sensor as in claim 9, further comprising:

disposing a heater on a heater side of a heater layer;

disposing the heater side of the heater layer adjacent to said third electrode; and disposing a third electrode layer between said third electrode and said heater layer.

11. A method for producing an oxygen sensor as in claim 9, further comprising:

disposing an outer electrode lead in electrical communication with said outer electrode; and disposing an inner electrode lead in electrical communication with said inner electrode.

* * * * *